United States Patent [19]

Garren

[11] Patent Number: 4,499,086

[45] Date of Patent: Feb. 12, 1985

[54] MEDICATION FOR TREATMENT OF POISON OAK IRRITATION AND INFLAMMATION

[76] Inventor: Frederick G. Garren, Unit 16, 2525 NE. Stephens, Roseburg, Oreg. 97470

[21] Appl. No.: 467,828

[22] Filed: Feb. 18, 1983

[51] Int. Cl.³ .............................................. A61K 35/78
[52] U.S. Cl. .................................. 424/195.1; 514/862
[58] Field of Search ........................................ 424/195

[56] References Cited

U.S. PATENT DOCUMENTS

| | | | |
|---|---|---|---|
| 2,254,051 | 8/1941 | Taylor | 424/195 |
| 2,552,896 | 5/1951 | Lee | 536/4.1 |
| 3,627,888 | 12/1971 | Salkin | 424/195 |
| 3,920,816 | 11/1975 | Seegall et al. | 424/195 |

OTHER PUBLICATIONS

The United States Pharmacopeia, 16th Rev., (1960), pp. 131 to 133.
The Merck Index, 9th Ed., (1976), p. 240.
Elias, Thomas S., "Trees of North America", (1980), pp. 738 to 753.
Peattie, Donald C., "A Natural History of Western Trees", (1953), pp. 638–640.
Remington's Pharmaceutical Sciences, 15th Ed., (1975), pp. 739 and 740.
Tyler, Varro E., et al., "Pharmacognosy", 8th Ed., (1981), pp. 55 to 60.
Lewis, Walter H. et al., "Medical Botany—Plants Affecting Man's Health", (1977), pp. 18, 39, 40, 280, 281, and 284.
Gault, S. Millar, "The Color Dictionary of Shrubs", (1976), p. 131.
Trease, George E., and William C. Evans, "Pharmacognosy", 10th Ed., (1971), pp. 54 to 57, 103, 122 to 127, 270, 271, 492 to 499 and 682 to 684.
Martindale-The Extra Pharmacopoeia, 27th Ed., London, (1977), pp. 1045, 1335 and 1336.
Lloyd, John Uri, "Pharmacopeial Vegetable Drugs, Chemicals and Preparations", vol. II, (1921), pp. 263 to 267.
Harlow, William M., and Ellwood S. Harrar, "Textbook of Dentrology", McGraw-Hill Book Co., 5th Ed., p. 421.
Home Remedies, C. E. Hidag, 1981, p. 12.

*Primary Examiner*—Jerome D. Goldberg
*Assistant Examiner*—John W. Rollins
*Attorney, Agent, or Firm*—Fisher, Christen & Sabol

[57] ABSTRACT

Therapeutic composition for the alleviation and curing of poison oak irritation and inflammation, respectively of the skin and/or mucous membranes. The medicant is composed of an aqueous extract from the leaves and buds of *Ceanothus thyrsiflorus,* otherwise known as California Lilac. The extract is prepared by steeping the leaves and buds in hot water.

2 Claims, No Drawings

MEDICATION FOR TREATMENT OF POISON OAK IRRITATION AND INFLAMMATION

BACKGROUND OF THE INVENTION

1. Field of the Invention

The invention relates to therapeutic compositions for the treatment and/or curing of poison oak irritation. The invention also relates to processes of manufacturing such therapeutic compositions, and to processes of using such therapeutic compositions.

2. Prior Art

Chemically speaking, the greatest interest in Ceanothus species has been in studying the complex peptide alkaloids, which occur mainly at every low concentrations in the rootbark of several species.

*Ceanothus americanus* leaf extracts have been employed in the United States of America as a sedative, for asthma, as an antispasmodic and as an expectorant. [Clark, A. H., Amer. J. Pharm., 147–156 (1926).] Rootbark extracts of such species have been employed by the Cherokee Indians as a panacea for a wide variety of illnesses, as early as the year 1700 [Clark]. Rootbark extracts have been widely employed to hasten blood clotting [Clark]. Such species is known in the vernacular as Jersey Tea, Red Root and Wild Snowball.

Aqueous and chloroform extracts of *C. americanus* roots have been reported to be devoid of antimalarial activity when administered orally and/or subcutaneously to chicks infected with *Plasmodium gallinaceum*. [Spencer, C. F., F. R. Koniuszy, E. F. Rogers, J. Shavel, Jr., N. R. Easton, E. A. Kaczka, F. A. Kuel, Jr., R. F. Phillips, A. Walti, K. Folkers, C. Malanga and A. O. Seeler, Lloydia, 10:145 (1947)].

Most pharmacological studies carried out on *C. americanus* have been directed toward verifying the alleged hemostatic or antihemorrhagic effects of such plant. The first studies of such type were reported in 1927 by Groot who administered a hydroalcoholic extract prepared from *C. americanus* rootbark to a number of human subjects orally and reported a marked reduction in blood coagulation time, which commenced about 15 minutes following administration and persisted for about one hour. [Groot, J. T., J. Pharmacol. Exp. Ther., 30:275–291 (1927).] Several other studies in humans have seemingly confirmed such anticoagulant effect, either employing hydroalcoholic, total alkaloids or semi-purified alkaloid extracts of *C. americanus* rootbark. [Tharaldsen, S. E. and J. Krawetz, Amer. J. Physiol., 79:545–552 (1927); Tharaldsen, C. E. and J. Krawetz, J. Ophth., Otol., Laryngol., 31:226–235 (1927); Payne, R. J., Ann. Otol. Rhin. Laryngol., 35:769–790 (1926); Taylor, G. C., Amer. J. Pharm., 99:214–232 (1927); and Gibbs, O. S., J. Pharmacol. Exp. Ther., 36:173–177 (1929).] The hydroalcoholic extract has been administered to several hundred human subjects and no side effects have been reported. The usual decrease in clotting time produced by the extract in humans was from 25 to 50 percent. [Tharaldsen et al. I; Tharaldsen et al. II; Payne; Taylor; and Gibbs.] Hydroalcoholic extracts of rootbark and alkaloid fractions have been administered orally and/or subcutaneously to rats, guinea pigs, rabbits and dogs, with decreases in clotting time reported in all cases. [Lynch, T. A. and T. S. Miya, Dissertation Abstracts, 27:562 (1966); Groot; Tharaldsen et al. I; Tharaldsen et al. II; and Payne.] A single report in 1929 showed no effect on coagulation time of a hydroalcoholic extract of rootbark following oral administration to several human subjects at a dose of 80 ml per subject. [Gibbs] The author attributed such discrepancy to inappropriate means of determining coagulation time in the earlier studies.

In an attempt to identify the substances responsible for the reduction in clotting time, the effects of a hydroalcoholic extract of rootbark were compared with those of the acidic and neutral fractions, following oral administration to rats. The latter fraction was found to be inactive, whereas the two former fractions were active. It was shown that oxalic, malonic, succinic, orthophosphoric and pyrophosphoric acids were present in the active acid fraction and that all of them produced a reduction in clotting time in vitro. [Lynch]

A hydroalcoholic extract of rootbark was administered intragastrically to dogs at a dose of 125 ml daily for 19 days. No acute nausea and/or vomiting was noted. Kidney function tests were carried out on the dogs and were found to be normal during the testing period. [Koppanyi, T., J. Amer. Pharm. Ass., 17:528–529 (1928).]

Ceanothic acid, a trierpene present in *C. americanus* rootbark, has been reported to have no effect on clotting time when administered to dogs intravenously at doses of 100 and 300 mg/kg. [Julian, P. L., J. Pikl and R. Dawson, J. Amer. Chem. Soc., 60:77–79 (1938).]

A hydroalcoholic extract of rootbark has been reported to elicit marked hypotensive activity following i.v. administration to anesthetized dogs with no apparent effect on the heart. [Groot] However, a later report indicated that the total alkaloid fraction of rootbark had no effect on dog blood pressure when administered at doses of less than 5.0 mg/kg. At doses of 5 to 10 mg/kg there was only a transient hypotensive response and a slight increase in heart rate. [Roscoe, C. W. and N. A. Hall, J. Amer. Pharm. Ass., Sci. Ed., 49:108–112 (1960)]

U.S. Pat. No. 2,254,051 teaches that a crystalline extract of *Ceanothus americanus* was a blood coagulant.

An uncharacterized alkaloid (m.p. 183°–186°) isolated from *C. americanus* rootbark has been extensively studied for its pharmacologic effects. [Manian, A. A. and L. D. Edwards, Dissertation Abstracts, 16:2479 (1956).] The alkaloid had no local anesthetic, antihistaminic or hemolytic effects in laboratory animals and it did not affect uterine tissue or the smooth muscle of cattle carotid arteries. In rats, it displayed an $LD_{50}$(i.v.) of 96.4 mg/kg and in mice 90 to 100 mg/kg (i.v.). No mortalities resulted following oral administration of the alkaloid to rats at doses up to 1.0 gm/kg. The alkaloid was hypotensive when administered to normotensive dogs, cats and rats and was anthypertensive in hypertensive rats. The electrocardiogram indicated that the hypotension could have resulted from a cumulative cardiotoxic action. In isolated heart preparations, the alkaloid produced coronary vasodilator effects at low doses (rat, guinea pig and rabbit hearts). At 5.0 mcg doses, the alkaloid produced positive chronotropic, inotropic and tonotropic effects on the isolated rat heart. At larger doses there was a negative inotropic and negative chronotropic effect, with cardiac arrest. The alkaloid produced a vasodilator effect in the perfused rat hind limb preparation. When administered, i.p. to rats at 50 mg/kg, the alkaloid produced an antisecretory effect on unstimulated gastric secretions. At doses of 50 to 100 mg/kg given by the intraperitoneal route to rats, the alkaloid produced an antidiuretic effect, but was devoid of this activity when administered orally. Daily dosing with the alkaloid for 45 days (i.p., rats), produced extensive fibrous connective tissue formation and petechiae in the mesenteries and small intestine. Histopathological studies indicated marked changes in the pancreas, and stomach and slight lesions in the adrenal glands, kidney and dorsal aorta. [Manian et al.]

Concerning the species *Ceanothus interrimus* Hook et Arn., water and chloroform extracts prepared from either the root or rootbark of this species were shown to be devoid of antimalarial activity when administered orally to chicks infected with *Pasmodium gallinaceium*. [Spencer et al.]

Concerning the species *Ceanothus velutinus* Dougl., in 1905, Rooney described cases of dermatitis in subjects exposed to *C. velutinus* leaves. [Rooney, California State J. Med., (1905).] Such was later confirmed experimentally, with the toxic substance(s) demonstrated to be present in the leaves or in an ether extract of the leaves. [Richards, L. W. and E. V. Lynn, J. Amer. Pharm. ASs., 23:332-336 (1934).] Aqueous extracts prepared from the leaves failed to produce dermatitis in humans. [Richards et al.] An ether-insoluble alkaloid extract prepared from *C. velutinus* roots was administered intraduodenally to anesthetized dogs at a dose of 10 mg/kg and was shown to have no effect on blood pressure. The ether-soluble alkaloids were also devoid of hypotensive activity. [Roscoe et al.]

BROAD DESCRIPTION OF THE INVENTION

An object of the invention is to provide a therapeutic composition or medicant for the alleviation and quicker curing of poison oak irritation and inflammation, respectively, of the skin and/or mucous membranes. Another object of the invention is to provide a process for the preparation of such therapeutic composition. A further object is to provide a process for the use of such therapeutic composition. Other objects and advantages of the invention are set out herein or are obvious herefrom to one ordinarily skilled in the art.

The objects and advantages of the invention are achieved by the compositions and process of the invention.

The invention involves the therapeutic or curative use of a therapeutically-active substance or substances from California Lilac leaves. The invention medication is used for the treatment of poison oak irritation of the skin, mucous membrances and the like. The invention medication quickly cures the areas affected by the poison oak, even if blisters and/or open sores are present. An important feature of the invention is the speeding up and enhancing of the curative process of the affected areas of the person.

The invention involves a therapeutic composition for the alleviation and speeding up of the curing of poison oak irritation and inflammation, respectively, of the skin and/or mucous membranes. The composition includes (a) a carrier and (b) an extract from the leaves and buds of *Ceanothus thyrsiflorus*. The extract contains one or more therapeutically active ingredients. *Ceanothus thyrsiflorus* is also known as California Lilac. Preferably carrier (a) is water and is preferably the water used to extract the active ingredients from the leaves and buds. The preferred composition can be in the form of an aqueous concentrate due to the removal of part of the water. The term "extract", as used herein, can be the extracted therapeutically or physiologically active (and unactive) ingredients themselves or the extracted active (and unactive) ingredients in the liquid extracting liquid.

The invention also involves the production process of extracting the solvent-soluble constituents of the leaves and/or buds of *Ceanothus thyrsiflorus* from the leaves and/or buds by means of a solvent or other liquid extractant. Preferably the leaves and/or buds of *Ceanothus thyrsiflorus* are admixed with hot water and the leaves and/or buds are steeped in the hot water. Preferably the hot water has a temperature of about 180° F. The steeping is preferably conducted for a period of about 7 to about 10 minutes. Preferably the mixture contains about 5 grams of the leaves and/or buds per pint of the water. The leaves and/or buds can be particulated before being steeped.

The invention also involves the process of alleviating and speeding up the curing of poison oak irritation and affliction, respectively, of the skin and/or mucous membranes which comprises treating, at least once, said irritated and afflicted areas of the skin and/or mucous membranes with the therapeutic composition of claim 2.

The subject species is the species *thyrsiflorus* of the genus Ceanothus, which is commonly known as the California Lilac.

DETAILED DESCRIPTION OF THE INVENTION

The invention medication for the cure of poison oak, composed of a compound of the herbal California Lilac, which when applied to the affected areas, causes almost immediate relief and cure. The invention product is prepared by the steeping of California Lilac buds and leaves, producing a liquid concentrate of variable potency, which is then applied to the poison oak. The applied medication causes an immediate healing process to set in, which rapidly accelerates the healing process so that the poison oak is healed within a fairly short time.

California Lilac is also known as Wild Lilac, Blueblossom, Blue Myrtle, Cascade (possible form of *C. thyrsiflurus*), *C. Mandocinensis* (hybrid) and *C. Repens* (a low spreading form of *C. thyrsiflorus*).

Blueblossom or *Ceanothus thyrsiflorus* Eschsch. is native to the Pacific Coast of the U.S., ranging from southwestern Oregon to central California. It grows in canyons and on shaded hillsides and slopes, usually at low elevations but up to 2,300 feet elevation. It occurs in redwood forests, mixed coniferous forests, and scrubby brushlands. The plants are of no known commercial importance, but the young twigs and leaves are an important food for mule deer. The light-brown wood is soft, and not strong. It is a branched large shrub or small tree growing to 20 feet, with a narrow, open crown. The truck is short, branching close to the ground. The bark is thin, (0.1 inch) thick, smooth becoming roughened with thin scales, reddish-brown. The branches are slender, upright and the brachlets are slender, spreading, angled, green and slightly hairy when young, becoming smooth and reddish-brown with age. Winter buds are small, covered with scales. The leaves are simple, alternate, and evergreen, being broadest near the middle or base to uniformly wide, 0.8-2 inches long, 0.5-1.1 inch wide, round to pointed at the tip, rounded to tapering at the base, finely gland-toothed along the margin, with 3 conspicuous main veins, dark green and smooth above, paler beneath. The flowers are light to deep blue, rarely white, bisexual, produced in many flowered, branched clusters 1.2-3.2 inches long, at the tips of the branchlets or in the junction of the upper leaves. The fruits are capsules, 3-lobed, nearly globe-shaped, 0.1–0.2 inch across, sticky, almost black, splitting open to release the smooth tiny seeds.

Any of the varieties of the species *Ceanothus thyrsiflorus* can be used. Preferably the variety *Ceanothus thyrsiflorus* Eschscholtz is used.

The genus Ceanothus is a member of the family Rhamnaceae or the "Buckthorn" family.

The leaves and buds can be extracted in that form or can first be particulated, for example, by chopping, grinding or the like. The extraction is preferbly done by using water, but any other suitable solvent can be used which extracts the therapeutically-active ingredient or ingredients. The extraction is preferably achieved by steeping the leaves and buds in hot water. The hot water usually has a temperature of 150° to 200° F., and preferably about 180° F. The steeping is conducted for a sufficient period of time to extract the active ingredient or ingredients from the leaves and buds. The preferred steeping time is 7 to 10 minutes.

Typically 1 to 20 grams, preferably about 5 grams, of the leaves and buds are used per pint of water during the steeping operation. Maceration can also be used.

The buds and leaves can be freshly-cut, non-freshly-cut and even in dried form. The leaves and buds should be cleaned before being used.

The water or other liquid solvent or extractant can be partially or completely removed from the liquid extraction. Solvent removal can be achieved by any suitable means, such as, refluxing. The solid extracted material can be removed by any suitable means such as filtration and centrifugation. Final drying can be done under vacuum or in a desiccator.

Extraction can also be achieved by the use of solvents or liquid extractants such as ethyl ether, methanol, ethanol, acetone, chloroform, methyl ethyl ketone, ethyl acetate and ethyl formate, provided the same active ingredient or ingredients are extracted by the non-aqueous solvent or liquid extractant as are extracted by water. Broadly, suitable ketones, suitable alcohols and suitable esters of a lower fatty acid can be used as the extractant or extracting agent. Mixtures of water and such non-aqueous solvents can be used.

Poison oak has a vine-like look but usually grows as a shrub 3 to 15 feet in height. It can be found in the form of a climbing vine (often on oak trees). Poison oak produces an irritant which is poisonous to the touch or contact and produces in many people a severe inflammation of the skin or dermatitis. The phytotoxins of poison oak cause skin irritation, swelling, blistering, erruption and itching. Smoke from the burning plants is toxic.

The extract from the leaves and buds of California Lilac can be used as a medicant in the form of a liquid mixture, a liquid concentrate, a solid extract, an ointment containing the extract, a gel containing the extract, a lotion containing the extract, an oil or soap solution containing the extract, etc. Thickening agents, e.g., tragacanth, can be present. For example, the liquid extract with or without the extracted leaves and buds can be applied to the affected skin areas. Preferably the extracted leaves and buds are first removed from the liquid extract, for example, by filtration or sieving.

Useful ointment bases or carriers include hard, soft or liquid paraffin bases, anhydrous lanolin, hydrophilic petrolatum, emulsion bases, and water-soluble bases prepared from polymers of ethylene glycol. Useful cream bases include emulsions of the oil-in-water or water-in-oil types. Useful paste bases include paraffin, starch and glycogelatin and contain a relatively large amount of powdered ingredients such as talc, calcium carbonate or zinc oxide. Useful aqueous gel bases include acacia, cellulose derivatives, gelatin, chondrus, gelatinized starch and tragacanth.

The extract can also be applied in the form of an aerosol, that is, as a space spray which disperses the extract as a finely divided spray with particles not exceeding about 50 microns and preferably as a surface-coating aerosol which produces a coarse or wet spray to coat the affected skin with a residual film. The propellant can be liquefied gases or compresses gases. The solid extract is dissolved in the liquefied gas or in a mixture of the gas and a suitable solvent. The aerosols include solutions, emulsions, suspensions, powders and semisolid preparations.

Atomizers can be used to apply aqueous solutions of the extract in the form of a spray to the mucous membranes of the nose or throat.

The extracted active ingredients can also be used in dry powdered form with or without an acceptable dry powdered pharmaceutical carrier (e.g., talc or chalk).

The medicant should be used one or more times (e.g., three) a day on the affected skin areas until the affected skin areas have been healed. Even only one treatment with the invention medicant improves the curing and decreases the curing time. No other medicant needs to be concurrently or subsequently used to effect quick and complete curing. The medicant is not taken or applied internally except on affected mucous membranes near the surface of body cavities, such as, the mouth, nose, etc., although the liquid medicant could be swabbed or otherwise applied to affected throat areas (caused by smoke from burning poison oak).

The exact nature of the above-described reaction is as yet unknown, due to the difficulty of isolating and dentifying the active component or components of the leaves and buds, especially since the very act of isolating a component might destroy factors dependent upon the interaction of various components at the same time. But the results of the invention demonstrate itself in the curative effects of the composition.

EXAMPLE

The ingredient for the medication was prepared from California Lilac leaves and buds, either dried or green, by steeping such leaves or buds in water at approximately 180° F. The mixture was 5 grams of such buds or leaves to a pint of water. The leaves and buds were steeped for a period of approximately 7 to 10 minutes and the cooled mixture was then applied to the affected poison oak areas. The medication cured the affected parts fairly soon depending on whether or not there were blisters. When blisters were present, it took a longer period of time to achieve healing. When the blisters had been scratched and open sores had resulted, a still longer period of time was required.

What is claimed is:

1. Process of alleviating and curing of poison oak irritation and affliction, respectively, of the skin or mucous membranes which comprises treating, at least once, said irritated or afflicted areas of the skin or mucous membranes with a therapeutic composition which comprises (a) a pharmaceutically acceptable carrier and (b) an extract from the leaves or buds or both of *Ceanothus thyrsiflorus* containing an effective amount of at least one therapeutically active ingredient which is effective in the alleviation of and speeding up of the curing of poison oak irritation or inflammation, respectively, of the skin or mucous membranes, said extract having been achieved using an extractant selected from the group consisting of water, ethyl ether, acetone, chloroform, methanol, ethanol, methyl ethyl ketone, ethyl acetate, ethyl formate, and a mixture of water and one of said extractants.

2. The process as claimed in claim 1 wherein carrier (a) is water and said extractant is water.

* * * * *